(12) United States Patent
Reust

(10) Patent No.: US 6,277,426 B1
(45) Date of Patent: *Aug. 21, 2001

(54) DAIRY PRODUCT AND PROCESS FOR MAKING

(75) Inventor: Hanspeter Reust, Gstaad (CH)

(73) Assignee: Swiss Alpine Power, Inc., College Park, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,444

(22) Filed: Sep. 18, 1998

(51) Int. Cl.⁷ ..................................... A23C 17/00
(52) U.S. Cl. ................... 426/583; 426/522; 426/580; 426/800; 426/801
(58) Field of Search ..................... 426/580, 583, 426/584, 586, 522, 800, 801, 804, 588

(56) References Cited

U.S. PATENT DOCUMENTS 3,896,241 * 7/1975 Malaspina et al. ................. 426/271
4,615,900 * 10/1986 Schenz et al. ...................... 426/590
5,912,040 * 6/1999 Girsh .................................. 426/583

FOREIGN PATENT DOCUMENTS

1452380 * 10/1976 (GB) .

OTHER PUBLICATIONS

Gulyaev–Zaitsev et al, AN 86(02):POO21 FSTA, abstracting Molochnaya Promyshlennost, 1984, No. 6, 15–17.*
Chojnowski et al, AN 81(01):P0227 FSTA, abstracting Roczniki Instytutu Przemyslu Mleczarskiego, 1979, 20(3), 61–70.*
Jindrichova et al, AN 79(08):H1227 FSTA, abstracting Czechoxlovak Patent, 184564, 1978.*

* cited by examiner

Primary Examiner—Leslie Wong
(74) Attorney, Agent, or Firm—Gabriel P. Katona L.L.P.

(57) ABSTRACT

A process for producing a whey product with extended shelf life, involving defatting the whey byproduct of cheesemaking, pasteurizing the defatted whey the first time, adding an adjuvant to the pasteurized whey, optionally adjusting the pH of the adjuvant-containing whey, pasteurizing the optionally pH-adjusted whey a second time, and recovering of the whey product.

17 Claims, No Drawings

DAIRY PRODUCT AND PROCESS FOR MAKING

FIELD OF THE INVENTION

The present invention relates to a dairy product which is useful as a low-fat dietary health food supplement in the form of a liquid or frozen whey beverage with an extended shelf life, and a cosmetic product of high whey content, and processes for making.

BACKGROUND

Cheese is prepared from milk that has been clotted, such as by the addition of an acid, inoculum, or rennet to form a curd. Whey (*Senim lactis*) is a cloudy liquid, the watery part of milk and is separated from the curd in the process of making cheese by centrifugation, decanting, or filtration. The most important ingredients of whey include lactose (and slight amounts of glucose and galactose), protein (albumin, and globulin), vitamin B (mainly riboflavin), and minerals and trace elements. Whey also has a milk-fat (triglyceride) content which can be either removed by centrifugation, or incorporated by homogenization. Whey is used as a valuable food supplement, but its shelf life is relatively short, therefore it has to be refrigerated and it has to be consumed rather quickly. Two major types of whey are available as protein sources, acid whey with a pH of <5.1 which is obtained from cottage cheese manufacture, and sweet whey with a pH of >5.6, resulting from the rennet-coagulated cheese manufacture. The composition of both of these whey varieties is slightly different, and variable, both of these varieties contain from about 0.7% to about 0.8% protein on a liquid basis, with whey proteins representing from about 10% to about 12% of the total whey solids.

Small quantities of condensed, deproteinated whey are used for making milk vinegar by fermentation with lactonitril. In the '50s there was a suggestion that the high vitamin content of whey would make it a suitable cosmetic ingredient, but in spite of that and its high nutritional value, liquid whey is generally considered to be a waste product and is mainly discarded due to its unattractive appearance, undesirable flavor and poor shelf life. Some cosmetic products have been made with small concentrations (max, up to about 20%) of liquid whey, their shelf life was unsatisfactory at higher whey solids concentrations.

Dry whey is a processed, usually freeze dried or spray dried powder which corresponds to about 15.4 times the weight of liquid whey. Some forms of whey powder are processed into concentrated protein isolates also being known under various trade names such as lactoferrin. These dry whey concentrates are generally used as an antimicrobial protein and an immuno-modulator, and usually contain over 25% protein. When the non-proteinaceous, low molecular weight constituents such as lactose, minerals, non-protein nitrogen and vitamins are removed, usually by physical separation (e.g. ultrafiltration, precipitation or dialysis), whey protein concentrates of over 90% protein can be obtained in the retentate. The high-protein concentrates are usually employed after pH adjustment in producing lactose, alcohol, single-cell protein, yeast, galactose, glucose, cattle feed and various pharmaceuticals. Except for the reduced moisture content, unprocessed dry whey usually retains the same constituents in the same proportion as in the fresh sweet or fresh acid whey from which it is dehydrated.

There have been proposed liquid beverages in the prior art based on whey, flavored, or otherwise, but in spite of their obvious low cost and high nutritional value they have achieved only limited acceptance. The problem has been mainly due to the fact that these beverages require refrigeration and also have a limited shelf life. Similarly, cosmetic products with a relatively low whey content were proposed, but they did not become commercially viable due to their limited shelf life mainly, because even with a low whey content their shelf life could not be extended by the use of conventional preservatives.

U.S. Pat. No. 3,922,375 discloses a pH-adjusted aqueous protein isolate solution prepared by mechanical separation from whey which can be incorporates into beverages and used as a clouding agent.

U.S. Pat. No. 4,086,367 describes a fruit-flavored, shelf stable and self-preserving, low-liquid content alimentary composition prepared from fruit flavors, finely dispersed fat particles enrobed in a fat enrobing agent that prevents coalescing of the fat particles by preventing fat-to-fat contact, wherein the enrobing agent is dried yeast or whey.

U.S. Pat. No. 4,615,900 discloses a method for producing an acidic dry-powdered beverage mix of a co-dried, pH adjusted protein or protein hydrolyzate-emulsifier complex.

U.S. Pat. No. 4,746,527 relates to a powder composition of fats, lactic proteins including whey, and lactose and other carbohydrates with gaseous cavities, that can be reconstructed to form a frothy beverage.

U.S. Pat. No. 4,790,998 relates to a clouding or creaming agent for acid-type beverages, from whey proteins and a lipid system.

U.S. Pat. No. 5,153,019 relates to a rice bran-honey beverage containing a whey protein concentrate.

U.S. Pat. No. 5,478,587 discloses a low-fat, substantially cholesterol and lactose-free, flavored dry dessert product containing whey protein or concentrates thereof.

French Pat. No. 2,665,056 discloses a drink for human or animal consumption from cow's or goat's milk with or without a flavorant.

German published patent application No. 2,535,904 relates to a beverage of fruit juice, whey, milk protein as a nutrient solution for lactic acid and yoghurt bacteria cultures, lactic acid from a highly cultured lactic acid bacteria culture, and other yoghurt bacteria cultures, with lactose as a sweetener, prepared by heating to 48° C. for optimal bacterium formation, and then heated to 85° C., and homogenized.

German published patent application No. 3,034,038 discloses a method for preparing a beverage formed by mixing whey with concentrated fruit juice, and then dispersing and homogenizing the mixture.

Soviet patent No. 805,987 discloses a soft drying from defatted milk that is filtered and flavored.

Soviet patent No. 1,829,902 relates to a whey-based beverage prepared by mixing it with a fruit juice and sugar syrup, and pasteurizing and clarifying by proteolytic fermentation, then filtration and deactivation of the ferment.

SUMMARY OF THE PRESENT INVENTION

It is an object of the present invention to provide processes for the utilization of whey byproducts by appropriate preservative treatment for enabling its use for various purposes utilizing its high vitamin an protein values and to improve its shelf life.

As used throughout the specification and the claims: (i) "whey" is generally liquid whey that is sweet whey or acid whey which is suitably and optionally ph adjusted to a defined maximum value; (ii) "frozen beverage" is an ice cream, sorbet, or flavored ice product made from liquid whey; (iii) "milk protein preparation" is a milk protein hydrolyzate, usually in a powder form, such as sold under the trade name hyprol dev. 2109 by quest international; (iv) "defatting" means the separation of the milkfats from the liquid part of the whey, usually by centrifugation, or any other technique known per se; and (v) "pasteurization" encompasses any process known per se for the antibacterially preservative treatment of alimentary products, such as by heat or radiation as may be accepted under desired end product parameters and local health regulations, but the term most suitably refers to pasteurization by the application of heat.

In accordance with the present invention a process is provided for the preparation of a whey product with extended shelf life, which comprises defatting the whey byproduct of cheesemaking, pasteurizing the defatted whey the first time, adding an adjuvant to the pasteurized whey, optionally adjusting the pH of the adjuvant-containing whey, pasteurizing the optionally pH-adjusted whey a second time, and recovering of the whey product. The whey is suitably defatted by centrifuging before pasteurizing the first time. The adjuvant is suitably a milk protein preparation, and can also be one or more flavorants.

The process for preparing the frozen beverage generally involves preparing a composition of a flavored whey product, with a yoghurt and/or cottage cheese, an artificial or natural sweetener, and citric acid or lemon juice, and freezing the composition to form the frozen beverage. The frozen beverage suitably also contains a fruit flavoring component, such as fruit pulp.

The cosmetic product of the present invention is especially characterized by an unprecedentedly high whey content in excess of 3% wt. solids basis (corresponding to about 45% fresh liquid whey), and contains a preservative such as an antimicrobic paraben combination product sold under the trade name Phenova W90, Phenoben W90, and Phenonip by Georges Walther AG, and/or imidazolidinyl urea. Suitably a liquid premix is prepared which can be used during its useful shelf life as a basic ingredient to add EDTA and citric acid and to formulate a cosmetic product therefrom in a manner known per se to cosmetic formulators.

DETAILED DISCLOSURE

Accordingly, it is an object of the present invention to provide various whey-based products, including liquid and frozen beverages and high whey-content cosmetics with a desirably long shelf life.

The fresh liquid natural sweet or acid whey from cheese manufacture is defatted, usually by centrifugation and, it is one advantage of the present invention that it does not require any homogenization. During centrifugal defatting any casein particles are also removed from the liquid. The minimal residual fat content is beneficially used to bring fat soluble vitamins into solution. The resulting fresh, defatted whey also includes lactose, protein (albumin and globulin) vitamins (A, B1, B2, B6, B12, pantothenic acid, C, biotin) and mineral traces (Ca, Mg, Na, K, P, Cl).

As fruit flavoring, optionally including fruit pulp or other fruit concentrate, water, natural or synthetic sweetener, aromatizing agents, and thickeners, and suitably a food acid such as citric acid are added if pH adjustment is needed, the whey mixture can develop a slight green coloration. If desired, this color can be masked or altered by appropriate selection of the additives, including any optional food coloring.

In addition to the double pasteurization the addition of a milk protein preparation assure the desired long shelf life of the liquid or frozen whey beverage of the present invention. In addition to its shelf life-extending effect, the use of the milk protein preparation, suitably has a probiotic, settling effect on the stomach and the digestive tract, particularly in the case of highly acidic liquids. The liquid beverage of the present invention has an average unrefrigerated shelf life of about 4 months.

The liquid whey beverage of the present invention has a pleasant fruit flavor which does not remind its consumer of milk. It tends to quiet hunger pangs. The drink is most suitably drunk when cooled to taste. On the average each liter of a suitably fruit flavored liquid beverage in accordance with the present invention, which has a high nutritional content, contains about 40 g lactose, 10 g fructose, 10 g protein, 7 g minerals, and has a nutritional value of 270 calories.

Pasteurization to destroy microorganisms and pathogens in the whey, can be carried out in any desired manner, with pasteurization by momentary heating to from about 71° C. to about 78° C., most suitably to about 72° C., followed by cooling to from about 20° C. to about 25° C. was found to be most suitable.

Suitably about 10% wt. to about 15% wt. fruit values are added to the whey and, depending on the resulting pH, the acidity can be optionally adjusted by citric acid to a maximum of about 4.5 to avoid the formation of mold and fermentation. Bottling is suitably carried out under aseptic conditions.

The frozen whey beverage can be, depending on its fat content, a whey based dairy ice, sorbet, or an ice cream. The starting mixture for preparing the dairy ice suitably comprises from about 3.5% to about 10% wt. added yoghurt and/or cottage cheese, from about 3.5% to about 10% wt. fruit flavor and/or fruit pulp, from about 30% to about 50% wt. of an artificial or natural sweetener or solution, from about 0.8% to about 7% wt. lemon juice or a corresponding amount of citric acid, together with from about 35% to about 65% wt. of the twice pasteurized liquid whey product of the present invention. The starting mixture for preparing the sorbet may contain no fruit flavoring at all, if desired, and up to twice as much of the added yoghurt and/or cottage cheese component.

Cosmetic products of all varieties can be prepared in accordance with the process of the present invention. The common feature of all of these cosmetic products is that they are made by the use of a whey-based premix, containing a very high percentage of whey. The premix made by the process of the present invention can be stored under refrigeration for extended periods of time. Generally up to a month.

In preparing the premix dry whey powder is suitably used. This is simply produced by the drying of fresh, natural whey, such as by spray drying or freeze drying. The dry whey powder residue is about 6.5% wt. of the starting liquid whey. The premix is made by mixing the powder with a liquid carrier, such as water, suitably deionized or distilled water, or even liquid whey. The mixture is heated, suitably to a temperature between about 50° C. and below its boiling point, suitably for a period of from about 20 minutes to about an hour. The heating can be suitably carried out at slightly reduced pressure, in one or more stages.

An essential ingredient of the premix is a paraben preservative, such as those sold under the trade names Phenova W90, Phenoben W90, and Phenonip, or a mixture of phenoxyethanol, with one or more of methyl-, ethyl-, propyl-, and butylparaben. Another essential ingredient of the premix is imidazolidinyl urea.

At the time of further using the premix made in accordance with the present invention for the formulating of a cosmetic product, citric acid and ethylenediamine tetraacetic acid (EDTA), or a salt thereof, such as the sodium salt, are added to the premix before or with the other conventional cosmetic ingredients. It has been found that for optimally long shelf life the presence of the 4 components is needed, namely the paraben preservative and the imidazolidinyl urea component in the premix, and the citric acid and EDTA or salt thereof in the end product.

The proportions of the essential ingredients of the premix and the two ingredients subsequently added during formulation, can vary according to the desired characteristics of the cosmetic end product, and can be determined for each particular kind of product by routine experimentation. Suitably the cosmetic end product contains from about 3% wt. to about 13% wt. whey powder (or from about 20% wt. to about 45% wt. whey powder based on the premix).

For example, a suitable aqueous body shampoo formulation contains, among other ingredients, 6% wt. whey powder, 0.8% Phenova W90, 0.15% wt. citric acid, and 0.12% wt. tetrasodium EDTA. A suitable day cream cosmetic formulation can contain 9% wt. whey powder, and 0.3% wt. each of Phenova W90 and imidazolidinyl urea, with 0.1% wt. each of citric acid and EDTA added to the premix in preparing the product. A suitable liquid soap composition is made with 6% wt. based on the products of whey powder, 0.8% wt. Phenova W90, 0.3% wt. imidazolidinyl urea, 0.12% wt. EDTA, and 0.020% wt. citric acid (with from about 0.08 to about 0.4% wt. each of the paraben composition and the imidazolidinyl urea, independently of each other, based on the premix).

If desired, some cosmetically beneficial additives, such as for example aloe barbadensis gel and jojoba oil can be added at the time when the finished cosmetic product is formulated. The finishing formulation of the cosmetic product itself is a conventional step per se which is familiar to skilled cosmetic formulators, and includes, according to the nature of the intended finished product, one or more of water, surfactant, fat, emulsifier, scouring compound, solvent, perfume and the like ingredients.

I claim:

1. A process for producing a nonfermented whey product with extended shelf life, which comprises defatting the whey byproduct of cheesemaking, pasteurizing the defatted whey the first time, adding a milk protein enriching adjuvant to the pasteurized whey, optionally adjusting the pH of the adjuvant-containing whey, pasteurizing the optionally pH-adjusted whey a second time, and recovering the nonfermented whey product.

2. The process of claim 1, further comprising defatting the whey by centrifuging before pasteurizing the first time.

3. The process of claim 1, wherein said product is a flavored liquid or frozen beverage, and said adjuvant is a milk protein preparation.

4. The process of claim 3, wherein said milk protein preparation is a milk protein hydrolyzate.

5. The process of claim 1, wherein the optional adjusting of the pH is carried out by optionally adding an alimentarily acceptable acid to the adjuvant containing whey to acidify it to a maximum pH of 4.5.

6. The process of claim 5, wherein said acid is citric acid.

7. The process of claim 4, wherein said adjuvant comprises a milk protein hydrolyzate and optionally a fruit flavor additive.

8. The process of claim 1, wherein said recovering of the whey product comprises cooling the pasteurized product to ambient temperature, and bottling the twice pasteurized product under aseptic conditions.

9. The process of claim 8, wherein said cooling is accomplished within a time period of under 30 seconds.

10. The process of claim 8, wherein said recovering further comprises adding one or more of dietary supplements to the product.

11. The process of claim 10, wherein said dietary supplement is one or more of a vitamin, a mineral supplement, and an amino acid.

12. The process of claim 8, wherein said recovering of the whey product further comprises adding a fruit flavored additive thereto.

13. The process of claim 3, wherein said frozen beverage comprises a dairy ice, a sorbet, or an ice cream.

14. The process of claim 13, wherein said sorbet further comprises yoghurt or cottage cheese, an artificial or natural sweetener, and citric acid or lemon juice, and said step of recovering the product comprises freezing the product to form a sorbet.

15. The process of claim 14, wherein said frozen beverage is a sorbet which comprises from about 7% to about 20% wt. yoghurt or cottage cheese, from about 35% to about 65% wt. of a twice pasteurized, defatted whey containing an adjuvant, from about 30% to about 50% wt. of said sweetener in liquid form as a syrup or a solution, and from about 0.8% to about 7% wt. lemon juice or a flavoringly corresponding amount of citric acid.

16. The process of claim 13, wherein said frozen beverage is a dairy ice, and comprises at least one of yoghurt and cottage cheese, fruit flavor or fruit pulp, an artificial or natural sweetener, and citric acid or lemon juice, and said step of recovering the product comprises freezing the product to form a dairy ice.

17. The process of claim 16, wherein said dairy ice comprises from about 3.5% to about 10% wt. yoghurt or cottage cheese, from about 3.5% to about 10% wt. fruit pulp or a flavoringly equivalent amount of a fruit flavorant, from about 35% to about 65% wt. of a twice pasteurized, defatted whey containing an adjuvant, from about 30% to about 50% wt. of said sweetener in liquid form as a syrup or a solution, and from about 0.8% to about 7% wt. lemon juice or a flavoringly corresponding amount of citric acid.

* * * * *